US010910507B2

(12) United States Patent
Huang et al.

(10) Patent No.: US 10,910,507 B2
(45) Date of Patent: Feb. 2, 2021

(54) SEMICONDUCTOR PACKAGE DEVICE AND METHOD OF MANUFACTURING THE SAME

(71) Applicant: Advanced Semiconductor Engineering, Inc., Kaohsiung (TW)

(72) Inventors: Cheng-Ling Huang, Kaohsiung (TW); Ying-Chung Chen, Kaohsiung (TW)

(73) Assignee: ADVANCED SEMICONDUCTOR ENGINEERING, INC., Kaohsiung (TW)

( * ) Notice: Subject to any disclaimer, the term of this patent is extended or adjusted under 35 U.S.C. 154(b) by 490 days.

(21) Appl. No.: 15/619,414

(22) Filed: Jun. 9, 2017

(65) Prior Publication Data
US 2018/0358501 A1  Dec. 13, 2018

(51) Int. Cl.
*H01L 31/16* (2006.01)
*A61B 5/00* (2006.01)
*A61B 5/0408* (2006.01)
*H01L 31/0203* (2014.01)

(52) U.S. Cl.
CPC ............ *H01L 31/16* (2013.01); *A61B 5/0082* (2013.01); *A61B 5/0408* (2013.01); *H01L 31/0203* (2013.01); *A61B 2562/0209* (2013.01); *A61B 2562/0238* (2013.01); *A61B 2562/06* (2013.01); *A61B 2562/185* (2013.01)

(58) Field of Classification Search
CPC ... H01L 31/0203; H01L 25/072; H01L 25/10; H01L 25/167; H01L 25/18; H01L 31/16; H01L 31/02366; H01L 25/041; H01L 25/042; A61B 2562/0209; A61B 5/0082; A61B 5/0408; A61B 2562/0238; A61B 2562/06; A61B 2562/185
See application file for complete search history.

(56) References Cited

U.S. PATENT DOCUMENTS

| 8,847,243 | B2 * | 9/2014 | Coffy | G01S 7/4813 |
| | | | | 257/81 |
| 9,905,722 | B1 * | 2/2018 | Chen | G01S 7/4813 |
| 10,177,268 | B2 * | 1/2019 | Chen | G01S 7/4813 |
| 2012/0248625 | A1 * | 10/2012 | Coffy | G01S 7/4813 |
| | | | | 257/774 |
| 2013/0075761 | A1 | 3/2013 | Akiyama | |

(Continued)

FOREIGN PATENT DOCUMENTS

TW    201316495 A    4/2013

OTHER PUBLICATIONS

Notice of Allowance from corresponding Taiwan Patent Application No. 107104230, dated Dec. 8, 2020, 4 pages.

(Continued)

*Primary Examiner* — Latanya N Crawford Eason
(74) *Attorney, Agent, or Firm* — Foley & Lardner LLP

(57) ABSTRACT

A semiconductor package device comprises a substrate, a light emitter, a light detector and a transparent conductive film. The substrate as a first surface and a second surface opposite to the first surface. The light emitter is disposed on the first surface of the substrate and has a light emission area adjacent to the first surface of the substrate. The light detector is disposed on the first surface of the substrate and has a light receiving area adjacent to the first surface of the substrate. The transparent conducting film is disposed on the second surface of the substrate.

20 Claims, 5 Drawing Sheets

(56) References Cited

U.S. PATENT DOCUMENTS

| | | |
|---|---|---|
| 2015/0243824 A1 | 8/2015 | Bhat et al. |
| 2015/0317553 A1 | 11/2015 | Pueschner et al. |
| 2015/0340409 A1 | 11/2015 | Popp et al. |
| 2015/0357505 A1 | 12/2015 | Chang et al. |

OTHER PUBLICATIONS

Search Report (with English Translation) from corresponding Taiwan Patent Application No. 107104230, dated Dec. 8, 2020, 2 pages.

* cited by examiner

SEMICONDUCTOR PACKAGE DEVICE AND METHOD OF MANUFACTURING THE SAME

BACKGROUND

1. Technical Field

The present disclosure relates to a semiconductor package device, and more particularly, to a semiconductor package device including an electrocardiography (ECG) detecting device.

2. Description of the Related Art

In an ECG detecting device, the ECG signal is measured using a light emitter and a light detector. In order to increase the precision and accuracy of the measurement result of the ECG, the ECG signal can be measured by both optical and electrical manners. In an ECG detecting device including both optical and electrical detecting components, the light emitter and the light detector are disposed on the substrate, and a conductive cover is placed on the substrate, which increase an overall size of the detecting device and the complexity for manufacturing the detecting device. In addition, in order to avoid cross-talk between the light emitter and the light detector, a light block wall is disposed on the substrate and between the light emitter and the light. However, the light emitted from the light emitter may be immediately received by the light detector, without propagating through a body, via an over-bleeding transparent molding compound under the light block wall, which may cause malfunction of the detecting device.

SUMMARY

In some embodiments, according to an aspect of the present disclosure, a semiconductor package device comprises a substrate, a light emitter, a light detector and a transparent conductive film. The substrate has a first surface and a second surface opposite to the first surface. The light emitter is disposed on the first surface of the substrate and has a light emission area adjacent to the first surface of the substrate. The light detector is disposed on the first surface of the substrate and has a light receiving area adjacent to the first surface of the substrate. The transparent conducting film is disposed on the second surface of the substrate. The semiconductor package device may comprise a light block element disposed within the substrate and between the light emitter and the light detector.

In some embodiments, according to another aspect of the present disclosure, a semiconductor package device comprises an opaque layer, a first electronic component, a substrate, and a transparent conductive film. The opaque layer has a first surface and a second surface opposite to the first surface. The first electronic component is disposed within the opaque layer and adjacent to the first surface of the opaque layer. At least a portion of an active surface of the first electronic component is exposed by the opaque layer. The substrate is disposed on the first surface of the opaque layer. The substrate is configured to transmit light. A transparent conducting film is disposed on the substrate. The semiconductor package device may further comprise a second electronic component disposed within the opaque layer and adjacent to the first surface of the opaque layer. At least a portion of an active surface of the second electronic component is exposed from the opaque layer. The active surface of the second electronic component is configured to receive a light emitted from the active surface of the first electronic component. The semiconductor package device may further comprise a light block element disposed within the substrate and between the first electronic component and the second electronic component.

In some embodiments, according to another aspect of the present disclosure, a method for detecting body information comprises: providing a substrate comprising a first conductive layer on a first surface of the substrate; detecting a first electric potential from the first conductive layer of the substrate that is in contact with a first portion of a body; emitting a light passing through the substrate to reach the first portion of the body by a light emitter; and detecting the light reflected from the first portion of the body by a light detector.

BRIEF DESCRIPTION OF THE DRAWINGS

Aspects of some embodiments of the present disclosure are best understood from the following detailed description when read with the accompanying figures. It is noted that various structures may not be drawn to scale, and dimensions of the various structures may be arbitrarily increased or reduced for clarity of discussion.

Figure 1A:
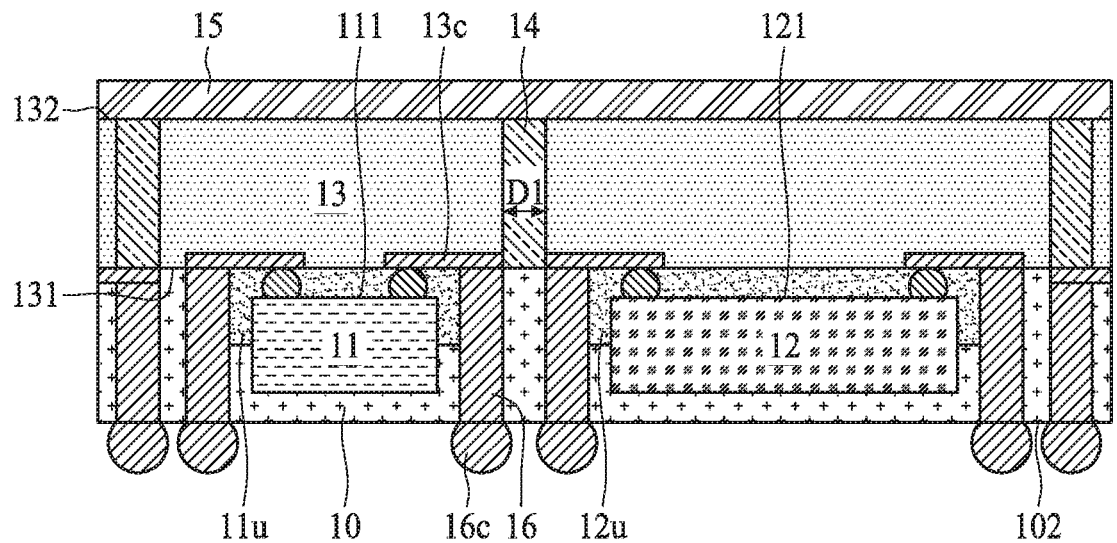
FIG. 1A illustrates a cross-sectional view of a semiconductor package device in accordance with some embodiments of the present disclosure.

Common reference numerals are used throughout the drawings and the detailed description to indicate the same or similar components. The present disclosure can be best understood from the following detailed description taken in conjunction with the accompanying drawings.

DETAILED DESCRIPTION

FIG. 1A illustrates a cross-sectional view of a semiconductor package device 1 in accordance with some embodiments of the present disclosure. The semiconductor package device 1 includes an opaque layer 10, electronic components 11, 12, a substrate 13, a light block element 14, a transparent conducting film 15 and at least one conductive element 16.

The substrate 13 has a surface 131 and a surface 132 opposite to the surface 131. In some embodiments, the surface 131 of the substrate 13 is referred to as a bottom surface or a first surface and the surface 132 of the substrate 13 is referred to as a top surface or a second surface. The material of the substrate 13 may be selected to allow the transmission of light emitted or received by the electronic components 11 and/or 12. In some embodiments, the substrate 13 is a glass substrate.

The electronic component 11 is disposed on a bottom surface 131 of the substrate 13. In some embodiments, the electronic component 11 may be a light emitter or a light emitting device, such as a light-emitting diode (LED) or other light emitting die. For example, the electronic component 11 may include, e.g., an LED, a laser diode, another device that may include one or more semiconductor layers, or a combination of two or more thereof. The semiconductor layers may include silicon, silicon carbide, gallium nitride, or any other semiconductor materials. The electronic component 11 can be connected to the substrate 13, for example, by way of flip-chip or wire-bonding techniques. The electronic component 11 has a light emission area 111 (also referred to as active surface) facing the bottom surface 131 of the substrate 13. The light emission area 111 of the electronic component 11 is covered or encapsulated by an underfill 11u. The material of the underfill 11u is selected to allow the transmission of light emitted by the electronic component 11. In some embodiments, the underfill 11u includes an epoxy resin.

The electronic component 12 is disposed on the bottom surface 131 of the substrate 13 and is physically separated from the electronic component 11. In some embodiments, the electronic component 12 may be a light detector which may be, e.g., a PIN diode, a photodiode, or a phototransistor. The electronic component 12 can be connected to the substrate 13, for example, by way of flip-chip or wire-bonding techniques. The electronic component 12 has a light receiving area 121 (also referred to as active surface) facing the bottom surface 131 of the substrate 13. The light receiving area 121 of the electronic component 12 is covered or encapsulated by an underfill 12u. The material of the underfill 12u is selected to allow the transmission of light received by the electronic component 12. In some embodiments, the underfill 12u includes an epoxy resin.

The opaque layer 10 is disposed on the bottom surface 131 of the substrate 13 to cover or encapsulate the electronic components 11, 12. The opaque layer 10 exposes the light emission area 111 of the electronic component 11 and the light receiving area 121 of the electronic component 12. In some embodiments, the opaque layer 10 can help preventing the light emitted by the electronic component 11 from being immediately transmitted to the electronic component 12 without propagating through a body. In some embodiments, the opaque layer 10 may be formed of, or at least includes, a black molding compound.

The transparent conducting film 15 is disposed on the top surface 132 of the substrate 13. The transparent conducting film 15 is formed of, or includes, an optically transparent, electrically conductive material. The transparent conducting film 15 allows the transmission of light emitted by the electronic component 11 and received by the electronic component 12. In some embodiments, the transparent conducting film 15 comprises a transparent conductive oxide (TCO) (e.g., indium tin oxide (ITO)), a conductive polymer, a metal grid, carbon nanotubes (CNTs), graphene, a nanowire mesh, an ultrathin metal film, or a combination of two or more thereof.

Figure 1B:
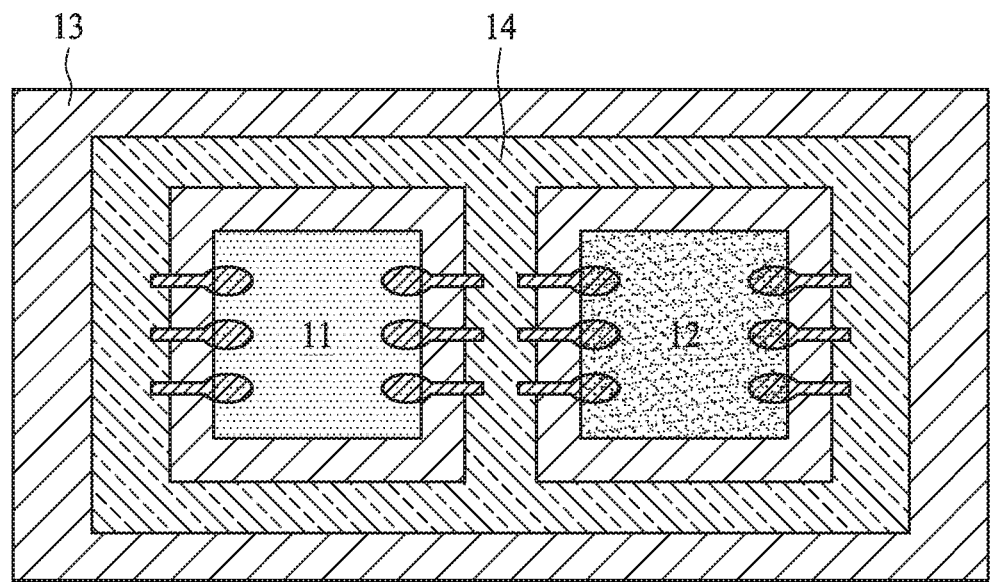
FIG. 1B illustrates a bottom view of a semiconductor package device in accordance with some embodiments of the present disclosure.

The light block element 14 is disposed within the substrate 13 and between the electronic component 11 and the electronic component 12. The light block element 14 is substantially opaque to prevent undesired light emitted by the electronic component 11 from being immediately transmitted to the electronic component 12 without propagating through a body. The light block element 14 is electrically conductive and penetrates the substrate 13 to electrically connect transparent conducting film 15 with a conductive pad 13c that is disposed on the bottom surface 131 of the substrate 13. In some embodiments, the light block element 14 is graphene. In some embodiments, as shown in FIG. 1B, which illustrates a bottom view of the semiconductor package device 1 shown in FIG. 1A, the light block element 14 may surround the electronic components 11 and 12 to prevent the electronic components 11 and 12 from being interfered by the undesired external light. In some embodiments, a width D1 of the light block element 14 is greater than, e.g., about 10 micrometer (μm), about 25 about 50 or about 75 μm to block the light efficiently.

The conductive element 16 penetrates the opaque layer 10 to electrically connect the conductive pad 13c on the bottom surface 131 of the substrate 13 to a conductive contact 16c on the bottom surface 102 of the opaque layer 10. Therefore, the transparent conducting film 15 on the top surface 132 of the substrate 13 and the conductive contact 16c on the bottom surface 102 of the opaque layer 10 are electrically connected via the light block element 14, the conductive pad 13c and the conductive element 16.

In order to measure the ECG signal accurately, an ECG detecting device including both optical and electrical detecting components can measure the ECG signal by both optical and electrical manners. In accordance with the embodiments shown in FIGS. 1A and 1B of the present disclosure, the active surfaces (e.g., the light emission area 111 and the light receiving area 121) of the electronic components 11 and 12 are disposed on a transparent substrate 13 (e.g., glass substrate) substrate) and the light block element 14 is embedded into the transparent substrate 13 and between the electronic components 11 and 12. In some embodiments, the semiconductor package device 1 include no additional substrate for holding back surfaces of the electronic components 11 and 12, and thus the overall size and manufacturing cost of the semiconductor package device 1 may be reduced. In addition, since the light block element 14 is embedded within the transparent substrate 13 and penetrates the substrate 13, the over-bleeding issue of the light block wall can be avoided, reduced, or eliminated.

In some embodiments, the semiconductor package device 1 may be used for measuring ECG signals. For example, during a process for measuring of the ECG of a human (or an animal), a first portion of the skin of the human contacts the transparent conducting film 15 or any other conductive contact electrically connected to the transparent conducting film 15; and a second portion of the skin of the human contacts the conductive contact 16c or any other conductive contact electrically connected to the conductive contact 16c. For example, one finger of the human contacts the transparent conducting film 15 while another finger of the human contacts the conductive contact 16c. The light emitted from the electronic component 11 is transmitted to the first portion of the skin of the human through the underfill 11u, the substrate 13 and the transparent conducting film 15. The electronic component 12 is used to detect or receive the light reflected from the first portion of the skin of the human through the transparent conducting film 15, the substrate 13 and the underfill 12u. The reflected light received by the electronic component 12 may be calculated or processed to obtain a first signal of the human. In addition, the transparent conducting film 15 (on which the first portion of the skin of the human is placed), the conductive contact 16c (on which the second portion of the skin of the human is placed) and the human body form a loop to obtain a second signal (e.g., electrical activities of the heart of the human). In some embodiments, the first signal measured in an optical manner and the second signal measured in an electrical manner can be calculated or processed to obtain an accurate ECG signal of the human. In some embodiments, the optical signal and the electrical signal are detected at the same time. Alternatively, the optical signal and the electrical signals may be detected separately at different points in time.

Figure 2:
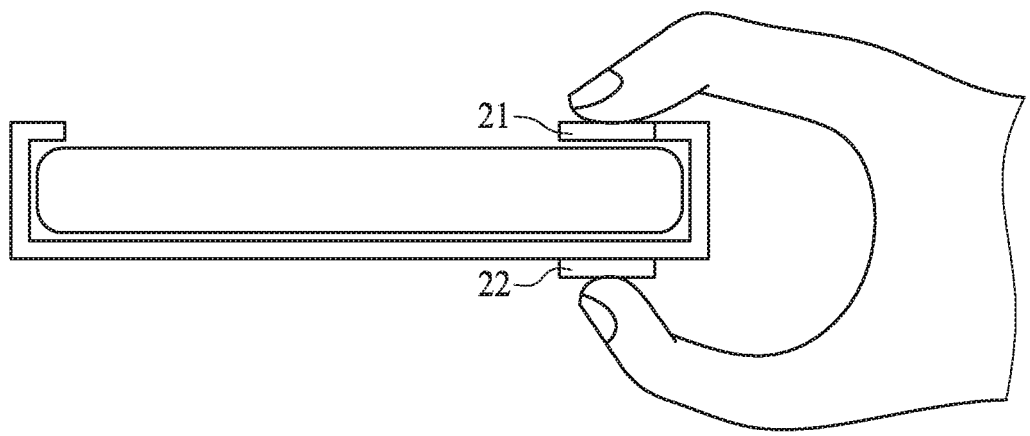
FIG. 2 illustrates an ECG detecting device in accordance with some embodiments of the present disclosure.

FIG. 2 illustrates an ECG detecting device 2 in accordance with some embodiments of the present disclosure. In some embodiments, the ECG detecting device 2 may be a smart phone, a tablet or any other suitable devices. The semiconductor package device 1 shown in FIG. 1A may be integrated into the ECG detecting device 2. The ECG detecting device 2 has a first contact 21 electrically connected with the transparent conducting film 15 of the semiconductor package device 1 and a second contact 22 electrically connected with the conductive contact 16c of the semiconductor package device 1. During the detection of the ECG signal, a finger of a human to be detected contacts the first contact 21 and another finger of the human contacts the second contact 22.

For a comparative ECG detecting device, two contacts may be placed on the same side of the ECG detecting device or may be separated far away. Therefore, a human to be tested has to use both hands for measuring the ECG signal. As shown in FIG. 2, since the first contact 21 and the second contact 22 are located on different sides of the ECG detecting device 2 and placed closely, the ECG signal can be detected by using a single hand.

FIGS. 3A, 3B, 3C, 3D, 3E, and 3F illustrate various stages of a semiconductor package manufacturing process, according to some embodiments of the present disclosure.

Figure 3A:
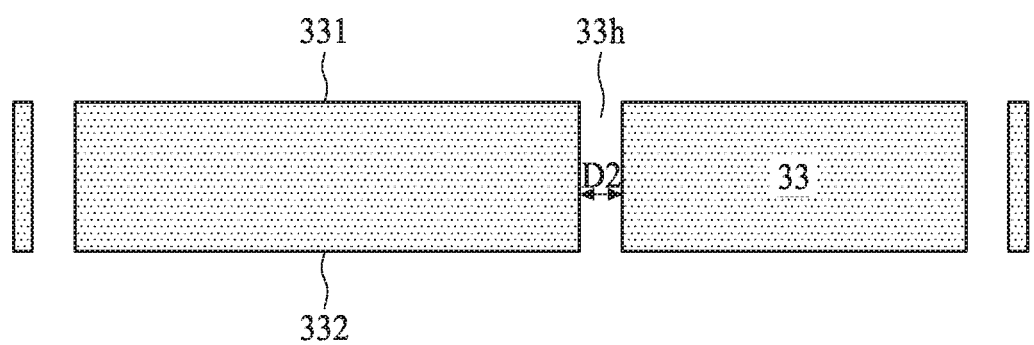
FIG. 3A illustrates one or more stages of a semiconductor package manufacturing process, according to some embodiments of the present disclosure.

Referring to FIG. 3A, a substrate 33 is provided. The substrate 33 has a surface 331 and a surface 332 opposite to the surface 331. In some embodiments, the substrate 33 is a glass substrate.

A plurality openings 33h are formed to penetrate the substrate 33. In some embodiments, the openings 33h can be formed by, e.g., routing, etching, laser drilling or other suitable processes. In some embodiments, a width D2 of the openings 33h is greater than, e.g., about 10 μm, about 25 μm, about 50 μm, or about 75 μm.

Figure 3B:
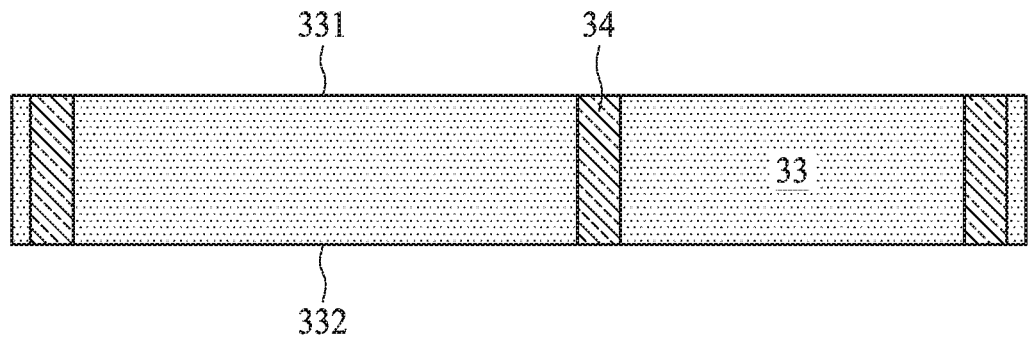
FIG. 3B illustrates one or more stages of a semiconductor package manufacturing process, according to some embodiments of the present disclosure.

Referring to FIG. 3B, an opaque, electrically conductive material is filled within the openings 33h of the substrate 33 to form a light block element 34. In some embodiments, the light block element 14 is formed of, or includes, graphene.

Figure 3C:
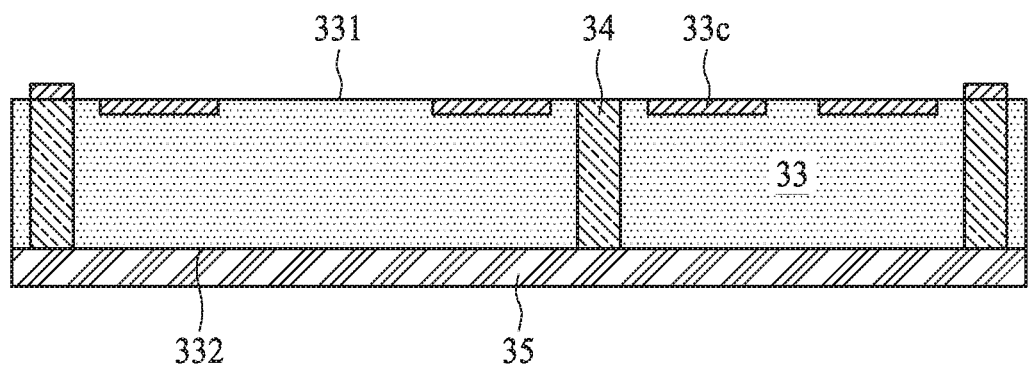
FIG. 3C illustrates one or more stages of a semiconductor package manufacturing process, according to some embodiments of the present disclosure.

Referring to FIG. 3C, conductive layers 33c are formed on the surface 331 of the substrate 33 and electrically connected with the light block element 34. The conductive layers 33c may be formed by, for example, sputtering, coating or other suitable processes. In some embodiments, the conductive layers 33c may be seed layers facilitating the formation of conductive pillars in the subsequent process.

A transparent conducting film 35 is formed on the surface 332 of the substrate 33 and electrically connected with the light block element 34. The transparent conducting film 35 is formed of optically transparent, electrically conductive material. In some embodiments, the transparent conducting film 35 comprises a TCO, a conductive polymer, a metal grid, CNTs, graphene, a nanowire mesh, an ultrathin metal film, or a combination of two or more thereof. In some embodiments, the transparent conducting film 35 can be formed by coating or other suitable processes.

Figure 3D:
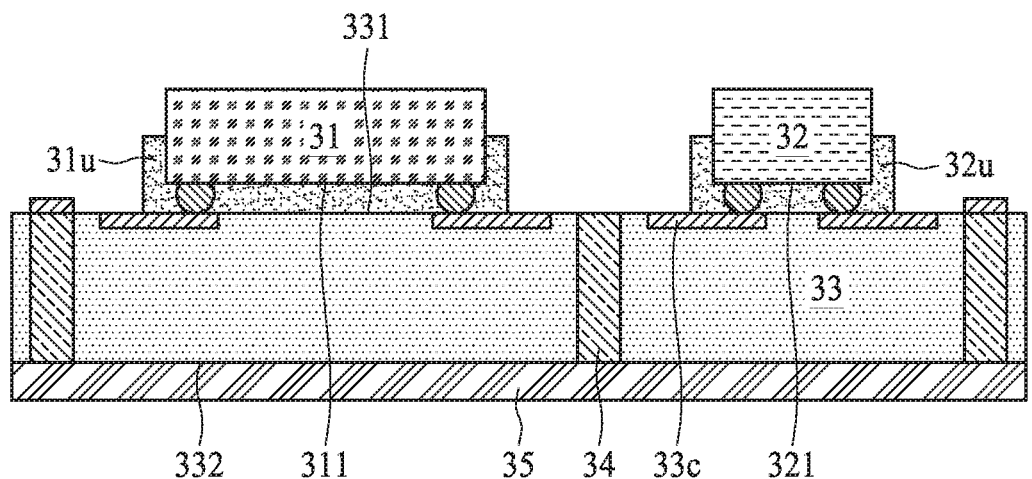
FIG. 3D illustrates one or more stages of a semiconductor package manufacturing process, according to some embodiments of the present disclosure.

Referring to FIG. 3D, an electronic component 31 is disposed on the surface 331 of the substrate 33 and electrically connected to the conductive layer 33c. In some embodiments, the electronic component 31 may be a light emitter or a light emitting device, such as an LED or other light emitting die. For example, the electronic component 31 may include an LED, a laser diode, or another device that may include one or more semiconductor layers. The semiconductor layers may include silicon, silicon carbide, gallium nitride, or any other semiconductor materials. The electronic component 31 can be connected to the substrate 33, for example, by way of flip-chip or wire-bonding techniques. The electronic component 31 has a light emission area 311 (also referred to as active surface) facing the surface 311 of the substrate 33.

An electronic component 32 is disposed on the surface 331 of the substrate 33 and electrically connected to the conductive layer 33c. In some embodiments, the electronic component 32 may be a light detector which may be, e.g., a PIN diode, a photodiode, or a phototransistor. The electronic component 32 can be connected to the substrate 33, for example, by way of flip-chip or wire-bonding techniques. The electronic component 32 has a light receiving area 321 (also referred to as active surface) facing the surface 331 of the substrate 33.

Underfills 31u and 32u are formed to respectively cover or encapsulate the light emission area 311 of the electronic component 31 and the light receiving area 321 of the electronic component 31. The materials of the underfills 31u and 32u are selected to allow the transmission of light emitted by the electronic component 11 and received by the electronic component 12. In some embodiments, the underfills 31u and 32u include an epoxy resin.

In some embodiments, after the operations shown in FIG. 3C, the semiconductor structure can be attached to a carrier through an adhesive (e.g., a tape) to facilitate the subsequent processes for placing the electronic components 31, 32 on the substrate 33. The carrier may be then removed after the operations shown in FIG. 3D.

Figure 3E:
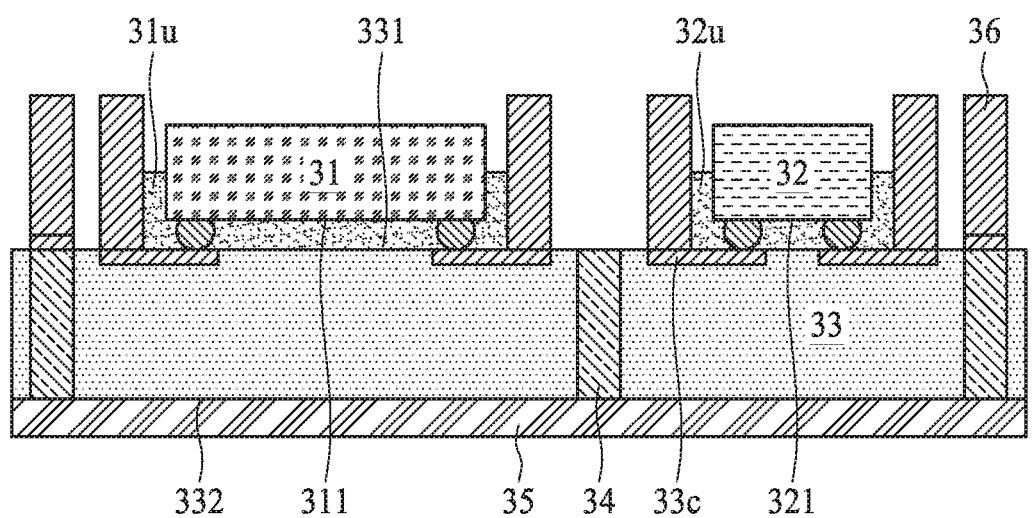
FIG. 3E illustrates one or more stages of a semiconductor package manufacturing process, according to some embodiments of the present disclosure.

Referring to FIG. 3E, conductive pillars 36 are formed on the conductive layers 33c of the substrate 33. In some embodiments, the conductive pillars 36 may be formed by the following operations: (i) placing a photoresist (e.g., a negative photoresist) on the surface 331 of the substrate 33; (ii) forming a plurality of openings at predetermined locations to expose the conductive layer 33c; (iii) filling conductive material (e.g., copper) into the openings by, for example, electroplating or other suitable processes; and (iv) removing the photoresist from the substrate 33.

Figure 3F:
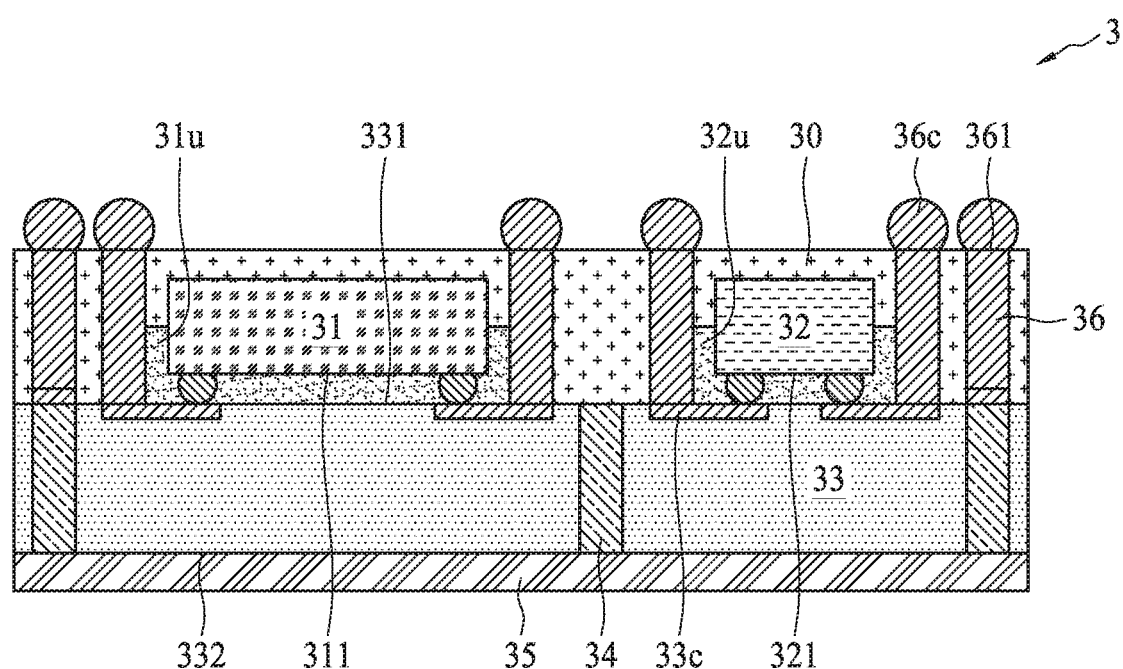
FIG. 3F illustrates one or more stages of a semiconductor package manufacturing process, according to some embodiments of the present disclosure.

Referring to FIG. 3F, an opaque layer 30 is formed on the surface 331 of the substrate 33 and encapsulates the electronic components 31, 32 and the conductive pillars 36. The opaque layer 30 exposes the light emission area 311 of the electronic component 31 and the light receiving area 321 of the electronic component 32. The opaque layer 30 can help preventing the light emitted by the electronic component 31 from being immediately transmitted to the electronic component 32 without propagating through a body. In some embodiments, the opaque layer 30 may be formed of, or may include, a black molding compound. In some embodiments, the opaque layer 30 may be formed by a molding technique, such as transfer molding or compression molding.

In some embodiments, after the formation of the opaque layer 30 a portion of the opaque layer 30 is removed to expose a top surface 361 of the conductive pillar 36 by, for example, grinding or other suitable processes.

Conductive contacts 36c (e.g., solder balls) are formed on the exposed portion of the top surface 361 of the conductive pillar 36 to form a semiconductor package device 3. In some embodiments, the semiconductor package device 3 is similar to the semiconductor package device 1 shown in FIG. 1A.

In the description of some embodiments, a component provided "on" another component can encompass cases where the former component is directly on (e.g., in physical contact with) the latter component, as well as cases where one or more intervening components are located between the former component and the latter component.

In the description of some embodiments, a component characterized as "light transmitting" or "transparent" can refer to such a component as having a light transmittance of at least 80%, such as at least 85% or at least 90%, over a relevant wavelength or a relevant range of wavelengths, such as a peak infrared wavelength or a range of infrared wavelengths emitted by a light emitter. In the description of some embodiments, a component characterized as "light shielding," "light blocking," or "opaque" can refer to such a component as having a light transmittance of no greater than 20%, such as no greater than 15% or no greater than 10%, over a relevant wavelength or a relevant range of wavelengths, such as a peak infrared wavelength or a range of infrared wavelengths emitted by a light emitter.

Additionally, amounts, ratios, and other numerical values are sometimes presented herein in a range format. It can be understood that such range formats are used for convenience and brevity, and should be understood flexibly to include not only numerical values explicitly specified as limits of a range, but also all individual numerical values or sub-ranges encompassed within that range as if each numerical value and sub-range is explicitly specified.

As used herein, the terms "approximately," "substantially," "substantial" and "about" are used to describe and account for small variations. When used in conjunction with an event or circumstance, the terms can refer to instances in which the event or circumstance occurs precisely as well as instances in which the event or circumstance occurs to a close approximation. For example, when used in conjunction with a numerical value, the terms can refer to a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

While the present disclosure has been described and illustrated with reference to specific embodiments thereof, these descriptions and illustrations do not limit the present disclosure. It will be clearly understood by those skilled in the art that various changes may be made, and equivalents may be substituted within the embodiments without departing from the true spirit and scope of the present disclosure as defined by the appended claims. The illustrations may not necessarily be drawn to scale. There may be distinctions between the artistic renditions in the present disclosure and the actual apparatus, due to variables in manufacturing processes and such. There may be other embodiments of the present disclosure which are not specifically illustrated. The specification and drawings are to be regarded as illustrative rather than restrictive. Modifications may be made to adapt a particular situation, material, composition of matter, method, or process to the objective, spirit and scope of the present disclosure. All such modifications are intended to be within the scope of the claims appended hereto. While the methods disclosed herein have been described with reference to particular operations performed in a particular order, it should be understood that these operations may be combined, sub-divided, or re-ordered to form an equivalent method without departing from the teachings of the present disclosure. Therefore, unless specifically indicated herein, the order and grouping of the operations are not limitations of the present disclosure.

What is claimed is:

1. A semiconductor package device, comprising:
    a substrate having a first surface and a second surface opposite to the first surface;
    a light emitter on the first surface of the substrate and having a light emission area adjacent to the first surface of the substrate;
    a light detector on the first surface of the substrate and having a light receiving area adjacent to the first surface of the substrate;
    a transparent conducting film on the second surface of the substrate, wherein the transparent conducting film is in contact with the second surface of the substrate;
    a first transparent layer between the light emitter and the first surface of the substrate; and
    a second transparent layer between the light detector and the first surface of the substrate, wherein the first transparent layer and the second transparent layer are underfills.

2. The semiconductor package device of claim 1, wherein the transparent conducting film comprises a transparent conductive oxide, a conductive polymer, a metal grid, carbon nanotubes, graphene, a nanowire mesh or an ultrathin metal film.

3. The semiconductor package device of claim 1, further comprising a light block element disposed within the substrate and between the light emitter and the light detector.

4. The semiconductor package device of claim 3, wherein the substrate further comprises a conductive layer adjacent to the first surface of the substrate, and the conductive layer is electrically connected to the transparent conducting film through the light block element.

5. The semiconductor package device of claim 3, wherein the light block element comprises graphene.

6. The semiconductor package device of claim 1, wherein the substrate is a glass substrate.

7. The semiconductor package device of claim 3, further comprising:
    an opaque layer on the first surface of the substrate to cover at least a portion of the light emitter, the light detector, the first transparent layer and the second transparent layer.

8. The semiconductor package device of claim 7, wherein the transparent conducting film is electrically connected to the opaque layer.

9. The semiconductor package device of claim 7, further comprising a conductive element electrically connecting a conductive pad on the substrate to a conductive contact on the opaque layer.

10. The semiconductor package device of claim 7, wherein the opaque layer comprises a molding compound.

11. A semiconductor package device, comprising:
    a substrate having a first surface and a second surface opposite to the first surface;
    a light emitter on the first surface of the substrate and having a light emission area adjacent to the first surface of the substrate;
    a light detector on the first surface of the substrate and having a light receiving area adjacent to the first surface of the substrate;

a transparent conducting film on the second surface of the substrate, wherein the transparent conducting film is in contact with the second surface of the substrate;

a first transparent layer between the light emitter and the first surface of the substrate;

a second transparent layer between the light detector and the first surface of the substrate; and an opaque layer on the first surface of the substrate to cover at least a portion of the light emitter, the light detector, the first transparent layer and the second transparent layer.

12. The semiconductor package device of claim 11, wherein the opaque layer comprises a molding compound.

13. The semiconductor package device of claim 11, wherein the substrate is a glass substrate.

14. The semiconductor package device of claim 11, wherein the transparent conducting film comprises a transparent conductive oxide, a conductive polymer, a metal grid, carbon nanotubes, graphene, a nanowire mesh or an ultrathin metal film.

15. The semiconductor package device of claim 11, further comprising a light block element disposed within the substrate and between the light emitter and the light detector.

16. The semiconductor package device of claim 15, wherein the substrate further comprises a conductive layer adjacent to the first surface of the substrate, and the conductive layer is electrically connected to the transparent conducting film through the light block element.

17. The semiconductor package device of claim 15, wherein the light block element comprises graphene.

18. The semiconductor package device of claim 11, wherein the transparent conducting film is electrically connected to the opaque layer.

19. The semiconductor package device of claim 15, further comprising a conductive element electrically connecting a conductive pad on the substrate to a conductive contact on the opaque layer.

20. The semiconductor package device of claim 19, wherein the transparent conducting film is electrically connected to the conductive contact via the light block element, the conductive pad and the conductive element.

* * * * *